United States Patent [19]

Matravers

[11] Patent Number: 4,894,222

[45] Date of Patent: Jan. 16, 1990

[54] WATERPROOF SUNSCREEN

[75] Inventor: Peter Matravers, San Marino, Calif.

[73] Assignee: Neutrogena Corporation, Los Angeles, Calif.

[21] Appl. No.: 177,090

[22] Filed: Apr. 4, 1988

[51] Int. Cl.$^4$ .................. A61K 7/027; A61K 7/40; A61K 7/42; A61K 7/48
[52] U.S. Cl. ...................................... 424/59; 424/60; 424/61; 424/63; 424/64; 514/844; 514/365; 514/873; 514/887; 514/969; 514/972
[58] Field of Search .................. 424/59; 514/969, 972

[56] References Cited

U.S. PATENT DOCUMENTS 4,303,639 12/1981 Vanderberghe .................. 614/873

OTHER PUBLICATIONS

Pascher, Dermatologic Formulary, 1957, pp. 69, 70, 66, 67, 68 and 40 to 42.

*Primary Examiner*—Dale R. Ore
*Attorney, Agent, or Firm*—Richard R. Mybeck

[57] ABSTRACT

A skin protective composition for topical application to mammalian skin for protection from water washing containing $C_{18}$–$C_{36}$ aliphatic wax and anhydrous starch as its principal active waterproofing agents disposed in a water-free carrier.

14 Claims, No Drawings

WATERPROOF SUNSCREEN

INTRODUCTION

The present invention relates geneally to a skin protective composition exhibitingg enhanced water repellency and more particularly to a new and improved composition containing aliphatic waxes and anhydrous hydrophobic starch in a pharmacologically acceptable water-free carrier and which, when admixed with our sunscreen and applied topically to exposed human skin, is surprisingly effective not only in screening ultraviolet radiation but waterproofing skin surfaces without tackiness, thereby enhancing user compliance and substantially reducing skin damage which otherwise would result from exposure to such solar radiation.

BACKGROUND OF THE INVENTION

While the need to protect human skin from solar radiation, particularly ultraviolet radiation, has been well documented during the past two decades, and a variety of preparations have been developed to provide varying degrees of "screening" or "blocking" therefrom, it has been found that the benefits of such compositions are readily lost when the user perspires or is engaged in water play which wahses off the protective coating thereby causing the benefits thereof to be quickly dissipated.

The need for a protective coating on the skin is essential because it is now proven that the sunlight contributes to aging and carcinogenesis by amplifying ultraviolet injury, altering the vasculature, producing diffusible mediators, changing histone binding properties, and/or damaging DNA repair processes. (See: Kaidbey, et al, Arch. Dermatol., 1982; 118 (5): 315-318.)

Ultraviolet and heat have been shown to synergistically denature human squamous buccal mucosal DNA. This work was carried out at 24° C., 32° C. (representing the temperature of indoor surface skin), and 42° C. (representing the surface skin temperature in bright sunlight at 26° North latitude). (See: Roth and London, J. Invest. Dermatol., 1977; 69; 368-372). Roth et al showed a positive linear relationship between DNA denaturation and irradiation temperature.

Principal considerations for selecting effective sunscreens include burning, tanning, and chronic changes such as, cancer, elastosis, wrinkling and pigmentary mottling. When considering the need for waterproofing protection, however, little information is available. Present sunscreens may protect against ultraviolet UVB and UVA. Unfortunately, they are usually non-substantive to skin and can easily be washed off by water or perspiration. As a result, many products on the market today will give consumers a false sense of security.

In an effort to address this problem, several compositions have been brought to market which contain a sunscreening agent and a water repellant in a cream or lotion base. However, in so far as they contribute certain desired properties, especially cosmetic properties to the skin, these compositions are not very elegant. They usually do not feel or appear like the conventional cosmetic creams or lotions made for other purposes and are usually very sticky, leaving an uncomfortable feel for the user. This tacky feel is usually caused by the polymer disposed in the sunscreen product in an attempt to effect water repellency. Therefore the conventional attempts had been the use of these plasticizers in cream/lotion bases with no work in the formulation of the cream/lotion base itself.

Moreover, the use of such polymers has additional drawbacks including "powdering" from too great a friability which further contributes to poor substantivity. Both cationic and anionic polymers can create this problem.

Accordingly, a real need exists in the industry for a waterproof composition especially useful with a sunscreen to provide effective protection for human skin from solar radiation with a magnitude of substantive integrity heretofore unavailable when anionic and cationic polymers are used to effect water repellency. It is toward this objective that the present invention is directed.

BRIEF SUMMARY OF THE INVENTION

The present invention is predicated upon the surprising discovery of a novel and unique composition of matter containing synthetic aliphatic waxes and anhydrous hydrophobic starch in a water-free base which may thereafter be admixed with any of a host of traditional ultraviolet (UV) absorbers. The composition, when used with sunscreening reagents and applied to mammalian skin, unexpectedly waterproofs the skin while blocking sun rays from the skin thereby protecting the skin from the severe adverse effects of the sun, irrespective of the activities of the user.

More particularly, the present invention is based on the discovery that the sunscreening agent may be anchored to the skin surface without using polymers by the use of a unique combination of synthetic aliphatic waxes and anhydrous hydrophobic starches disposed in a water-free carrier such, for example, as mineral oil and/or aliphatic esters.

This new composition, when used in a topical application, has many advantages including the creation of a water barrier; effective water repellency; strong resistance to being washed off; physiological inertness; non-irritancy and stability; and an elegant silky feel without tackiness.

Therefore, the principal objectives of this invention is to use the above mentioned advantages to formulate an even more superior sunscreen than has heretofore been obtainable. Specifically, the present invention provides improved sun protection through superior water repellency, improved duration of its protection, and a more elegant silky feel on the skin, than any conventional product of this kind on the market today.

Accordingly, a prime object of the present invention is to provide, without the use of tacky polymeric materials, a new and improved composition containing synthetic aliphatic waxes (e.g., Suncrowax ™ available from Croda, Inc., New York) and anhydrous hydrophobic starch (e.g., Dry Flo ®, available from National Starch and Chemicals Co., Bridgewater, N.J.) and which, when topically applied to human skin provides a waterproofing or water repellent action sufficient to maintain the active block reagents in operative relationship to the skin over periods of time and reduce the skin damage which would otherwise result from long exposure to unblocked radiation when the sunscreen is washed away and leaves the skin surface unprotected.

A further object of the present invention is to provide a new and improved topically applied water repellent sunscreen composition which is non-toxic, easy to apply, cosmetically acceptable, has no adverse effect on clothing worn therewith, and demonstrates an unexpected propensity to protect mammalian skin from the adverse effects of solar radiation.

Another object of the present invention is to provide a new and improved topically applied waterproof skin protective base composition which is compatible with conventional UV-A and UV-B sunscreen reagents and can be readily admixed therewith to provide a novel multifaceted product for long term protection from solar radiation, even when the user is engaged in water sports.

Still another object of the present invention is to provide methods of protecting the skin of human and like susceptible animals from the adverse effects of exposure to solar radiation and avoiding premature removal resulting from contact with water.

These and still further objects as shall hereinafter appear are readily fulfilled by the present invention in a remarkably unexpected manner as will be readily discerned from the following detailed description of an exemplary embodiment thereof.

DESCRIPTION OF THE PREFERRED EMBODIMENTS

The present invention is directed to a skin protective composition for long lasting topical application to the skin of humans and like susceptible animals (herein "mammals") having the unexpected ability to deter and prevent solar radiation from causing dermal destruction and cancer. The base compositions of the present invention is not only compatible with the conventional reagents employed to block and screen solar radiation but it is one which provides an unexpected quantum of water repellency thereby protecting the active reagents from premature removal by action of water thereupon.

The key to the present invention is a base composition which is not only a compatible vehicle for most approved sunscreens and blockers, but which creates a water resistant coating or film upon the human skin when topically applied thereto and retains its operaive position thereupon even when the wearer thereof perspires profusely or is splashing into and out of the water into the course of an outing to the ocean, lake, pond, pool or the like.

More particularly the key ingredients of the present composition are a synthetic aliphatic wax, that is, a high molecular weight $C_{18}-C_{36}$ saturated synthetic fatty acid wax such as Syncrowax ™, or an equivalent synthetic wax developed for use in cosmetics, admixed with an anhydrous hydrophobic starch such as Dry Flo ® (aluminum starch octenylsuccinate).

The anhydrous hydrophobic starches have been found to be extremely resistant to wetting by water while retaining the capacity of starch to absorb moisture without swelling.

In combination with the synthetic waxes described above, e.g., Syncrowax ™, a composition is created which unexpectedly obtains film-forming and water barrier properties far superior to the polymers heretofore employed as waterproofing agents. Further, no flasking or leaching of the sunscreen occurs. A further advantage arises from the unexpected permeability of the film to perspiration without wash off.

The base combination of the present invention consists of an aliphatic synthetic wax and an anhydrous hydrophobic starch, for example, Syncrowax ™ and Dry Flo ®, as its essential ingredients which are disposed in pharmacologically acceptable water-free extending medium which adapts said agents for application to the skin. Conventional ultraviolet screens or absorbers are then admixed therewithin as will hereinafter appear. The resulting compositions can be either solid or liquid in form. The compositions of the present invention can also be incorporated into various cosmetic and personal care products such as hand and body lotions, ointments, lip balm products, facial cosmetics, diaper creams, ostomy creams and the like.

The amount of $C_{18}-C_{36}$ saturated synthetic fatty acid wax and anhydrous hydrophobic starch present in the water-free base composition hereof may vary greatly. Preferably, the synthetic aliphatic wax will range from about one to about 10% by weight of the total composition and the anhydrous hydrophobic starch will vary from about three to about 30% by weight.

In a preferred practice, one or more other agents such as the conventional UV-A and UV-B absorbers, opaquers such as titanium, zinc or ferric oxide and the like may be added to the base composition. Greater amounts of these optional agents may be incorporated into various products limited only by processing and economic considerations and the amount of screen desired.

Other agents or constituents which may be used as the water-free extending medium to replace the mineral or vegetable oils indicated above for the base compositions of the present invention, include lanolin; vaseline; glycerol; triglycerides of fatty acids; polyethylene glycols; oxyethylenated fatty alcohols; esters such as isopropyl palmitate; myristate and stearate; silicone oils; oleyl oleate and butyl stearate; animal oils; fatty alcohols; glycerol monostearate, and organic and mineral waxes. These other constituents are generally used in an amount of about 10 to 96% by weight of the total formulation.

Among the cosmetic ingredients which may also be used in the composition of the present invention are: thickeners, softeners, superfatting agents, emollients, as well as preservatives, silicones, perfumes or any other compatible ingredients usually employed in cosmetics.

The following film-forming agents, polymers, and cosmetic resins may be employed when product design considerations warrant their inclusion, namely: polyvinylpyrrolidone, vinylpyrrolidone/vinyl acetate copolymers in which the monomer ratios are from 70/30 to 30/70, vinyl acetate/unsaturated carboxylic acid copolymers such as a copolymer containing 90% of vinyl acetate and 10% of crotonic acid; terpolymers of methyl methacrylate/stearyl methacrylate/dimethylaminoethyl methacrylate; completely quaternised with dimethyl sulphate, the monomers being used particularly in the ratio 20/23/57; and a terpolymer of vinyl acetate/allyl stearate/allyloxyacetic acid, especially in the ratio of 80/15/5; maleic anhydride/methyl vinyl ether copolymers such as those commercially referred to as "Gantrez AN" as well as the ethyl, isopropyl and butyl esters of these copolymers, and maleic anhydride/butyl vinyl ether copolymers. It is of course understood that these polymers which produces a sticky or tacky feel in conventional cream/lotion bases will be smooth and silky when used in this invention.

For topical application, sunscreen compositions must be non-toxic and non-irritating to the skin tissue and capable of application to the skin as a uniform continuous film. In addition, the active sunscreening agents must be chemically stable and in particular must be resistant to chemical and photodegradation when on the skin as well as resistant to absorption through the skin. Suitable ultraviolet absorbing sunscreening agents useful in the practice of the present invention include, oxybenzone (2-hydroxy-4-methoxy-benzophenone); dioxybenzone (2,2'-dihydroxy-4-methoxybenzophenone); amino benzoic acid; cinoxate (2-ethoxyethyl-p-methoxycinnamate); diethanolamine-p-methoxycinnamate; digalloyl trioleate ethyl 4-bis(hydroxy-propyl-)aminobenzoate; 2-ethylhexyl-2-cyano-3,3-diphenylacrylate; ethylhexyl-p-methoxycinnamate; 2-ethylhexyl salicylate; glyceryl aminobenzoate; homosalate (3,3,5-tri-methylcyclohexyl salicylate); triethanolamine salicylate; 2-phenylbenzimidazole-5-sulfonic acid; sulisobenzone (2-hydroxy-4-methoxybenzophenone-5-sulfonic acid); Padimate A (amyl p-dimethylaminobenzoate); Padimate 0 (octyl dimethyl para aminobenzoate); 4-t-butyl-4'-methoxy-dibenzoylmethane; the combination of 2-hydroxyl-1,4-naphthoquinone with dihydroxyacetone; and menthyl anthranilate.

Each of the foregoing compounds has been used alone or in combination with others in various sunscreen compositions and been found to provide varying sun protecting factors (SPF) when evaluated in human subject utilizing standard solar simulator tests.

The sunscreen material to be used herein to provide ultraviolet-A (320–400 nm) protection will be selected from the group comprising the pentyl and 2-ethylhexyl esters of 4-(dimethylamino) benzoic acid; dioxybenzone; ethylhexyl-p-methoxy-cinnamate; ethyl 4-bis(hydroxypropyl)aminobenzoate; 3,3,5-trimethylcyclohexyl salicylate; 2-ethylhexyl-2-cyano-3,3-diphenylacrylate; 2-ethylhexyl salicylate; 4-t-butyl-4'-methoxydibenzoylmethane and mixtures thereof. The sunscreen material is present in an amounts ranging from 1.0% to 20.0%, preferably 4.0% to 11.0% by weight of the total composition.

In one practice of the present invention, a suitably sized stainless steel tank is charged with mineral oil and the dual mixers (the sweep rotating at about 10 RPM clockwise while the turbine rotates at about 12 RPM counterclockwise) are activated.

Next, the batch is heated to 110° C. and, while heating, Syncrowax TM is added (sweep at 14 RPM and turbine at 24 RPM) until it is completely and homogeneously dispersed.

With the mixers at the speed indicated, an ultraviolet A absorber, such as benzophenone-3, is introduced and completely dissolved into the batch.

Next, the anhydrous hydrophobic starch (Dry Flo ®) is added to the batch while the mixers are maintained at the higher speed and the temperature is maintained above 78°–80° C. for one hour.

Added next, with stirring, is a suitable antioxidant such as dl-alpha tocopherol and suitable cosmetic additives such as cyclomethicone and the like.

The batch is then cooled at a rate of about 0.5° C./minute until a temperature of 25°–27° C. is reached. The batch, subject to Quality Control approval is now ready for packaging.

Using the foregoing procedure, compositions embodying the present invention were prepared as shown below, the ingredients other than synthetic aliphatic wax and anhydrous hydrophobic starch being shown as representative.

| Ingredient | wt/wt percent |
|---|---|
| Mineral Oil | 43.5–93.4 |
| Octyl methoxycinnamate | 1–7.5 |
| Glyceryl Tribehenate and | 1–10 |
| Calcium Behenate (Trade: Syncrowax TM HRS-C) | |
| Benzophenone-3 | 1–5 |
| Cyclomethicone | 0.5–3.0 |
| dl-alpha tocopherol | 0.1–1.0 |
| Anhydrous Starch (Dry Flo ®) | 3–30 |

The several compositions produced in accordance with the present invention were applied to human skin and measured for water repellency using the protocol described in Example 8.

As used in the Examples, a number of the synthetic waxes found especially useful in the present invention are identified by the tradename Syncrowax TM. All of these waxes are based in a $C_{18}$–$C_{36}$ saturated synthetic fatty acid wax and exhibit characteristics such as thermoplastic/crystalline properties which are similar to the natural waxes. The synthetic waxes employed herein are respectively designated "HRS-C" which identifies glyceryl tribehenate and calcium behenate; "ERL-C" which identifies the ethylene glycol ester of $C_{18}$–$C_{36}$ wax fatty acid; and "HGL-C" which identifies the glyceride ester of $C_{18}$–$C_{36}$ wax fatty acids. (See: CTFA Cosmetic Ingredient Dictionary, 3rd Edition, The Cosmetic, Toiletry and Fragrance Association, Inc., Washington, D.C. 20005).

To further illustrate the present invention, and not by way of limitation, the following examples are presented.

EXAMPLE 1

Mineral oil is placed in a suitably sized vessel heated to 110° C. and admixed. Next the synthetic aliphatic wax is added to the mineral oil and blended to a uniform consistency and composition. At this time the desired UV block is added to the extant mixture and thoroughly blended therewith and, while the temperature is maintained above 70°–80° C., the anhydrous hydrophobic starch is introduced with continued stirring. Any additional materials such as antioxidants, cosmetic additives and the like are then added as necessary and blended throughout the mixture.

The mixing time, temperature, and number of phases is, of course, dictated by the particular materials used. All such mixing is done in the conventional manner.

EXAMPLE 2

Using the procedure described in Example 1, a waterproof sun blocker was prepared having the following formula in weight percent:

| Ingredient | |
|---|---|
| Mineral Oil | 18.5–89.9 |
| Anhydrous Starch | 3–30 |
| Isopropyl Palmitate | 1–20 |
| PEG-7 glyceryl cocoate | 1–5 |
| Cetearyl Isononanoate | 1–5 |
| Octyl Methoxycinnamate | 1–7.5 |
| Benzophenone 3 | 1–5 |
| Phenyl dimethicone | 1–3 |
| dl-alpha tocopherol | .1–1 |
| Syncrowax TM HRS-C | 1–5 |

EXAMPLE 3

Using the procedure of Example 1, compositions embodying the present invention were prepared using a combination of synthetic waxes as shown below. Additional blockers such as TiO$_2$ and mica can be used with decreasing tackiness.

| Ingredient | wt/wt % |
|---|---|
| Mineral Oil | 34.5–90.4 |
| Octyl methoxycinnamate | 1–7.5 |
| Syncrowax TM HRS-C | 1–4 |
| Mica | 0.5–5 |
| Titanium Dioxide | 0.5–4 |
| Anhydrous Starch | 3–30 |
| Benzophenone-3 | 1–5 |
| Cyclomethicone | 0.5–3.0 |
| dl-alpha tocopherol | 0.1–1.0 |
| Syncrowax TM HGL-C | 1–3 |
| Syncrowax TM ERL-C | 1–3 |

EXAMPLE 4

Using the procedure of Example 1, an anhydrous translucent sun blocker was prepared having the following formula:

| 2 ethylhexyl stearate | 10–17 |
|---|---|
| Mineral Oil | 42.9–81 |
| Syncrowax TM HRS-C | 3–8 |
| Lanolin | 1–5 |
| Anhydrous Starch | 1–5 |
| Silica | 1–8 |
| Silicone Oil | 0.5–5 |
| dl-alpha tocopherol | 0.5–4 |
| Octyl Methoxycinnamate | 1–7.5 |
| Benzophenone 3 | 1–5 |
| Oleyl Alcohol | 1–3 |

EXAMPLE 5

Using the procedure as described in Example 1, a waterproof hand cream without sunscreen was prepared having the following formula (weight percent):

| Mineral Oil | 44.0–85.50 |
|---|---|
| C$_{12-15}$ Alcohol Benzoate | 5.0–20 |
| Syncrowax TM HGL-C | 1.0– 5 |
| dl-alpha tocopherol | .5– 1 |
| Anhydrous Starch | 3.0–20 |
| Cyclomethicone | 5.0–10 |

EXAMPLE 6

Using the procedure of Example 1, a waterproof diaper cream skin preparation was prepared having the following formula (in weight percent):

| C$_{10-30}$ Cholesterol Lanosterol | 10.0 |
|---|---|
| Anhydrous Starch | 10.0 |
| Emulsifying wax NF | 7.5 |
| Mineral Oil | 47.5 |
| Syncrowax TM HRS-C | 10.0 |
| PVP/Eicosene copolymer | 2.0 |
| dl-alpha Tocopherol | 2.0 |
| Dimethicone | 3.5 |
| Cyclomethicone | 7.5 |

EXAMPLE 7

Using the procedure of Example 1, a waterproof lip balm containing sunscreen was prepared having the formula (in weight percent):

| Mineral oil | 7.0 |
|---|---|
| Castor Oil | 6.0 |
| 2 ethylhexyl stearate | 4.4 |
| Oleyl Alcohol | 8.5 |
| Syncrowax TM HRS-C | 7.5 |
| Anhydrous Starch | 7.5 |
| Dimethicone | 2.0 |
| Octyl Methoxycinnamate | 7.5 |
| Octyl Salicylate | 5.0 |
| Menthyl Anthrinolate | 5.0 |

EXAMPLE 8

Using the procedure of Example 1, a sunscreen preparation was prepared having the following formula in weight percent:

| Mineral Oil | 47.3 |
|---|---|
| Syncrowax TM HRS-C | 1.5 |
| Syncrowax TM HGL-C | 0.5 |
| Syncrowax TM ERL-C | 0.5 |
| Stearalkonium hectorite and propylene carbonate | 4.0 |
| C$_{12-15}$ Alcohols benzoate | 9.0 |
| Benzophenone-3 | 4.2 |
| PEG-7 Glycerol Cocoate | 2.0 |
| Cetearyl Isononanoate | 1.0 |
| Octylmethoxy cinnamate | 7.4 |
| dl-alpha tocopherol | 0.1 |
| Dimethicone | 6.0 |
| Silica | 6.5 |
| Anhydrous Starch (Dry Flo ®) | 10.0 |

EXAMPLE 9

Tests were performed according to the procedures and the criteria outlined in the "Proposed Monograph for OTC Sunscreen Drug Products" issued by the F.D.A. on Aug. 25, 1978 (43 Fed. Reg. 166 at 38206-38269).

The purpose of the tests was to determine the Sun Protection Factor (SPF) efficacy on the skin of human subjects, before and after a total of 40 minutes and 80 minutes of water immersion.

The wet control test material, Johnson & Johnson SUNDOWN TM moderate (SPF=4), and the static control, 8% Homosalate, were prepared according to FDA Specifications (Fed. Reg., Ibid at 38259). The test product was prepared according to Example 8.

The light source was a Solar Ultraviolet Simulator, Model 10S (Fed. Reg., Ibid at 38260) consisting of a 150 watt Xenon arc lamp with all required optical elements and a regulated power supply.

A total of twenty fair skinned subjects (3 male, 17 female; Age range 20 to 53) with skin types I, II, and III were placed on test.

Testing was performed using the following procedures.

Test Site Inspection.

The physical examination determined the presence of sunburn, suntan, scars, active dermal lesions, and uneven skin tones on the areas of the back to be tested. The presence of nevi, blemishes or moles was acceptable if they would not interfere with the study results. Excess hair on the back, if present, was shaved.

Test Site Area.

A test site area served as an area for determining the subject's Minimal Erythema Dose (MED) after application of either the sunscreen product or for determining the subject's MED of unprotected skin (control site). The subject's MED is the time of exposure that produces the minimally perceptible erythema at 16 to 24 hr post-exposure. The area to be tested was the back between the beltline and the scapulae (shoulder blade) and lateral to midline. The test site areas were horizontal or vertical, and rectangular or square. Each test site area for applying a product or standard control was 50 cm sq. These test sites were outlined with gentian violet while the person to be tested was in an upright position.

Test Subsite Area.

Each test site area of the test was divided into five subsite test areas that were at least 1 cm sq. For subjects #1-5, three test site areas were used for the test material: one for before water immersion and one for after 80 minute water immersion. For subjects #6-20, for the test material and for the wet control, two test site areas were used: one for before water immersion and one for after 80 minute water immersion. Placement of test site areas were randomized among the 20 subjects. One additional test site area was used for 8% HMS SPF determination on each subject as per FDA Proposed Monograph.

Application of the Test Material.

To insure standardized reporting and to define a product's Sun Protection Factor (SPF) value, the application of the product is expressed on a weight basis per unit area which establishes a standard film. The test sunscreen product and the sunscreen standard application is 2 mg/cm sq or 2 ul/cm sq. The 50 cm sq test site area requires 100 mg of a product or 100 ul (assuming a specific gravity of 1) to obtain a standard 2 mg/cm sq test application. For the test product, a cream, the viscosity is such that the material was weighed and applied to the appropriate areas by spreading with a finger cot.

Waiting Period.

Before exposing the test site areas after applying a product, a waiting period of at least 15 minutes was employed.

Test Site Irradiation.

A series of UV light exposure (units of time) were administered to the subsites on each subject with the solar simulator. One series of exposures was administered to the untreated, unprotected skin to determine the MED. The MED is the time of exposure that produces the minimally perceptible erythema at 16 to 24 hour post-exposure. The MED of the subject's unprotected skin was determined prior to the test day, then again on the test day.

Each of the protected test sites (controls and/or test sunscreen product) were also exposed to UV light. The standard time intervals selected are a geometric series represented by (1.25)n, wherein each exposure time interval is 25 percent greater than the previous time. (The reason for using the geometric sequence of UV exposure is to maintain the same relative uncertainty, expressed as a constant percentage, independent of the subject's sensitivity to UV light, regardless of whether the subject has a high or low MED). The exact series of exposures to be given was determined by the MED of the unprotected skin.

For subjects #1-5, after UV irradiation of one test site each for both the test sunscreen and the above-cited control sunscreens, each subject entered the whirlpool for 20 minute; whirlpool agitation was at a moderate level. This was followed by a 20 minute rest period, followed by a second 20 minute period in the whirlpool. Care was taken and each subject was continuously monitored to insure that the "after" test site areas were untouched. At the conclusion of the 40 minute immersion, the test sites were air dried without toweling. The second protected test site of the test sunscreen was then exposed to UV light, using the identical method and series of exposures used for the "before" light irradiation. Each subject again entered the whirlpool for 20 minutes followed by a 20 minutes rest period, followed by a second 20 minute period in the whirlpool. At the conclusion of this 40 minute immersion, the test sites were air dried without toweling. The third protected test site of the test sunscreen and the second protected test site of the above-cited wet control sunscreen were then exposed to UV light, using the identical method and series of exposures used for the "before" UV light irradiation.

For subjects #6-20, after UV irradiation of one test site each for both the test sunscreen and the above-cited control sunscreens, each subject entered the whirlpool for 20 minutes; whirlpool agitation was at a moderate level. This was followed by a 20 minute rest period, followed by a third 20 minute rest period, followed by a fourth 20 minute period in the whirlpool Care was taken and each subject was continuously monitored to insure that the "after" test site areas were touched. At the conclusion of the 80 minutes water test, the test sites were air dried without toweling. The second protected test site of the appropriate test sunscreen and of the above-cited wet control were then exposed to UV light, using the identical method and series of exposures used for the "before" UV light irradiation.

Each subject reported back at 16 to 24 hour post-exposure, at which time each test site area was read to determine the MED of both the unprotected and the protected skin.

For both the test sites irradiated prior to water immersion and the test sites irradiated after 40 and 80 minute water immersion, the SPF of the test sunscreen is then calculated from the exposure time interval required to produce the MED of the protected skin, and from the exposure time interval required to produce the MED of the unprotected skin (control site), i.e.,

| SPF | - | MED Protected Skin |
|-----|---|--------------------|
|     |   | MED Unprotected Skin |

Results and Conclusions.

No adverse reactions were observed in any of the subjects who were tested as per the testing procedures described above. The Sun Protection Factor (SPF) value for the sunscreen, after 40 minutes immersion (5 subjects), and after 80 minute immersion (20 subjects) as well as for the controls (20 subjects), are as follows:

| Product | SPF | SPF Labeling Category |
|---------|-----|----------------------|
| Test Material | | |
| Before Immersion | 18.84 | 15.00 or greater (Ultra) |
| After 40 min. Immersion | 18.75 | 15.00 or greater (Ultra) |
| After 80 min. Immersion | 16.35 | 15.00 or greater (Ultra) |
| Controls | | |
| J & J SUNDOWN Moderate | | |
| Before Immersion | 5.00 | 4.00 to 5.99 (Moderate) |
| After 80 min. Immersion | 4.60 | 4.00 to 5.99 (Moderate) |
| 8% Homosalate | 4.40 | 4.00 to 5.99 (Moderate) |

From the foregoing, it is apparent that an invention has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended here.

Accordingly, what is claimed is:

1. A composition of matter for waterproofing mammalian skin containing in weight percent from about 1 to about 10 percent $C_{18}$–$C_{36}$ saturated synthetic fatty acid wax, from 3 to about 30 percent anhydrous hydrophobic starch dispersed in about 60 to about 96 percent of pharmacologically acceptable water-free carrier.

2. A composition of matter according to claim 1 in which said carrier is a mineral or vegetable oil or aliphatic/branched chain ester.

3. A composition of matter according to claim 1 in which said carrier is an anhydrous solvent.

4. A composition of matter according to claim 1 containing up to about 20% by weight of UV-A and UV-B blockers.

5. A composition of matter according to claim 2 containing up to about 20% by weight of UV-A and UV-B blockers.

6. A composition of matter according to claim 3 containing up to about 20% of UV-A and UV-B blockers.

7. A method of protecting and waterproofing mammalian skin from the harmful effects of solar radiation having a wave length of from 700–2600 nanometers comprising applying to such mammalian skin an effective amount of a preparation containing, in weight percent, from about 1 to about 10 percent $C_{18}$–$C_{36}$ saturated synthetic fatty acid wax and from about 1 to about 30 percent anhydrous hydrophobic starch, each being dispersed in a pharmacologically acceptable water-free carrier and admixed with an ultraviolet blocking agent.

8. A method of protecting mammalian skin according to claim 7 in which said carrier is an anhydrous ointment.

9. A method of protecting mammalian skin according to claim 7 in which said carrier is an anhydrous solvent.

10. A method of protecting mammalian skin according to claim 7 in which said carrier is an oil.

11. A method of protecting mammalian skin from the harmful effects of solar radiation having a wave length of from 700 up to 2600 nanometers comprising applying to such mammalian skin an effective amount of a preparation containing in weight percent, from about 1 to about 10 percent $C_{18}$–$C_{36}$ saturated synthetic fatty acid wax, from about 1 to about 30 percent anhydrous anhydrous starch, from about 1 to about 20 percent UV-A and UV-B blockers, each dispersed in a pharmacologically acceptable water-free carrier.

12. A method of protecting mammalian skin according to claim 11 in which said carrier is a solvent.

13. A method of protecting mammalian skin according to claim 11 in which said carrier is mineral oil.

14. A method of protecting mammalian skin according to claim 7 in which said carrier is an anhydrous cream.

* * * * *